(12) United States Patent
Treado et al.

(10) Patent No.: US 11,499,912 B2
(45) Date of Patent: Nov. 15, 2022

(54) SYSTEMS AND METHODS OF COVERT IDENTIFICATION

(71) Applicant: CHEMIMAGE CORPORATION, Pittsburgh, PA (US)

(72) Inventors: Patrick J. Treado, Pittsburgh, PA (US); David W. Caudle, Vandergrift, PA (US); Matthew P. Nelson, Pittsburgh, PA (US); Shawna Tazik, Pittsburgh, PA (US)

(73) Assignee: CHEMIMAGE CORPORATION, Pittsburgh, PA (US)

(*) Notice: Subject to any disclaimer, the term of this patent is extended or adjusted under 35 U.S.C. 154(b) by 47 days.

(21) Appl. No.: 16/737,597

(22) Filed: Jan. 8, 2020

(65) Prior Publication Data

US 2022/0277535 A1 Sep. 1, 2022

Related U.S. Application Data

(60) Provisional application No. 62/789,826, filed on Jan. 8, 2019.

(51) Int. Cl.
*G01N 21/27* (2006.01)

(52) U.S. Cl.
CPC ........... *G01N 21/272* (2013.01); *G01N 21/27* (2013.01)

(58) Field of Classification Search
CPC .............................. G01N 21/272; G01N 21/27
USPC ........................................................ 356/300
See application file for complete search history.

(56) References Cited

U.S. PATENT DOCUMENTS

| | | | | | |
|---|---|---|---|---|---|
| 5,459,470 | A | * | 10/1995 | Wootton | G01S 17/74 342/6 |
| 5,686,722 | A | * | 11/1997 | Dubois | G01S 17/74 398/118 |
| 6,493,123 | B1 | * | 12/2002 | Mansell | H04B 10/2587 342/45 |
| 6,795,174 | B1 | * | 9/2004 | Miller | G01S 17/74 244/3.13 |
| 2004/0173680 | A1 | | 9/2004 | Mossberg et al. | |
| 2005/0255599 | A1 | | 11/2005 | Wang et al. | |
| 2006/0028644 | A1 | | 2/2006 | Gardner, Jr. et al. | |
| 2013/0155402 | A1 | | 6/2013 | Walton et al. | |
| 2013/0201469 | A1 | | 8/2013 | Treado et al. | |
| 2013/0296710 | A1 | | 11/2013 | Zuzak et al. | |
| 2013/0321813 | A1 | | 12/2013 | Treado et al. | |

(Continued)

FOREIGN PATENT DOCUMENTS

| | | |
|---|---|---|
| EP | 3352145 A1 | 7/2018 |
| WO | 199701156 A1 | 1/1997 |

(Continued)

*Primary Examiner* — Sunghee Y Gray
(74) *Attorney, Agent, or Firm* — DLA Piper LLP (US)

(57) ABSTRACT

In order to avoid friendly fire incidents in the combat theater, novel covert identification systems and methods of identifying friendly forces are provided. The systems include at least a spectroscopic imaging device and a marker that interact with each other by using a synchronized, predetermined filter tuning sequence. The filter tuning sequence enables interacted photons to wavelength hop according to the predetermined tuning sequence. As a result, the covert identification system allows friendly forces to clearly identify each while avoiding detection by enemy forces that employ conventional broadband and night vision sensors.

18 Claims, 1 Drawing Sheet

(56) References Cited

U.S. PATENT DOCUMENTS

2014/0349337 A1 11/2014 Dasari et al.
2015/0160136 A1 6/2015 Natan et al.

FOREIGN PATENT DOCUMENTS

| WO | 2014140431 A1 | 9/2014 |
| WO | 2015128635 A1 | 9/2015 |
| WO | 2017102722 A1 | 6/2017 |

* cited by examiner

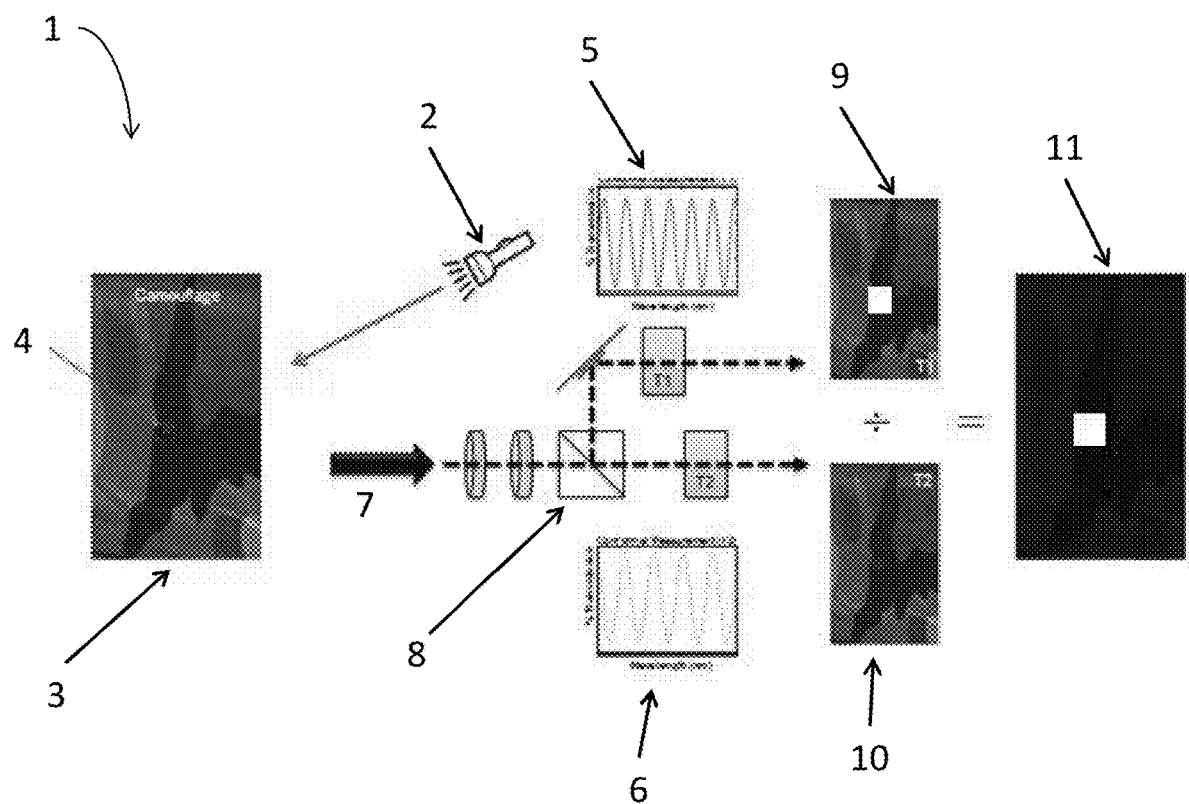

SYSTEMS AND METHODS OF COVERT IDENTIFICATION

CROSS REFERENCE TO RELATED APPLICATIONS

This application claims priority to U.S. Provisional Application No. 62/789,826 filed on Jan. 8, 2019, the entire contents of which is incorporated by reference.

BACKGROUND

Friendly fire is typically an accidental attack by military forces on their own forces, allied forces, neutral forces, or civilians. Such friendly fire is a longstanding challenge for military forces but recently has become more severe in modern warfare with the proliferation of powerful ranged weapons including piloted aircraft, autonomous (drone) aircraft, artillery, rockets, missiles, and firearms. Besides the weapons employed, modern warfare also carries significant risk of friendly fire as more conflicts are fought unconventionally. War zones are increasingly ill-defined and include mixtures of regular armed forces, special operations forces, allied forces, local militia forces, irregular insurgent forces, and civilians, often in chaotic urban environments. All of these factors make target identification difficult and require improvements in equipment and techniques to avoid friendly fire.

Avoiding friendly fire is especially difficult when the military force is a covert force, even more so at night or in reduced visibility. The covert force must be able to identify friendly forces without revealing its own location to enemy forces. Currently, the U.S. military and its allies employ infrared (IR) emitting and reflecting devices for Friendly Forces Identification (FFI), which are invisible to the naked eye and many cameras. However, the proliferation of third generation night vision devices (NVDs) and other electro-optic infrared (EO/IR) sensors means that both regular and irregular military forces have improved abilities to detect U.S. and allied forces' operations and communications in the visible, IR, longwave infrared (LWIR), shortwave infrared (SWIR), and midwave infrared (MWIR) electromagnetic radiation bands. Conventional FFI equipment also has the drawback of not being reconfigurable because it uses fixed frequencies that are provided by IR light emitting diodes (LED), chemiluminescence (chemlights being known informally as "glow sticks"), and IR reflective and retroreflective patches. This lack of reconfigurability means that if enemy forces discover the FFI techniques of friendly forces, the friendly forces are unable to adapt their equipment to avoid detection.

There is a need for FFI devices and techniques that permit covert identification of friendly forces while remaining resilient and reconfigurable in the field. The FFI devices should remain undetectable to enemy broadband sensors such as NVDs and EO/IR sensors that are now available to regular and irregular military forces around the world.

SUMMARY

The disclosure describes a covert identification system and methods of covert identification. In particular, the covert identification system and methods are designed to permit friendly forces to locate and identify other friendly forces, neutral forces, and/or civilians and distinguish them from hostile forces.

In one embodiment, there is a covert identification system comprising: a marker that includes at least one of a liquid crystal tunable filter (LCTF) and a conformal filter and which reflects interacted photons that have interacted with the LCTF or the conformal filter, a spectroscopic imaging device that includes at least one of a LCTF and a conformal filter and which is configured to receive the interacted photons, and wherein the LCTF or conformal filter of the spectroscopic imaging device operates in a pattern that corresponds to the pattern of the LCTF or conformal filter in the marker so that the spectroscopic imaging device can accurately distinguish between light that has interacted with the conformal filter and light that has not interacted with the marker.

In another embodiment, the covert identification system further comprises a light source that is configured to illuminate the marker.

In another embodiment, the light source for illuminating the marker emits spectrum selected from the group consisting of about 180-380 nm (UV), about 700-2500 nm (NIR), about 850-1800 nm (SWIR), about 650-1100 nm (MWIR), about 400-1100 nm (VIS-NIR), about 1200-2450 nm (LWIR), and combinations of the above ranges.

In another embodiment, the covert identification system does not include a light source for illuminating the marker, and during operation, the marker is illuminated by an external light source.

In another embodiment, the marker further includes a marker processor that is configured to control at least one of the LCTF or the conformal filter of the marker.

In another embodiment, the marker processor is configured to control at least one of the LCTF or the conformal filter of the marker to thereby encrypt the interacted photons.

In another embodiment, the spectroscopic imaging device further including a spectroscopic processor that is configured to control at least one LCTF or conformal filter of the spectroscopic imaging device.

In another embodiment, the spectroscopic processor is configured to control at least one of the LCTF or the conformal filter of the spectroscopic imaging device to thereby decrypt the interacted photons.

In another embodiment, the covert identification system further comprises a power source.

In one embodiment, there is a method of covert identification comprising: illuminating with photons a marker that includes at least one of a liquid crystal tunable filter (LCTF) and a conformal filter so that the marker reflects interacted photons that have interacted with the LCTF or the conformal filter, receiving interacted photons with a spectroscopic imaging device, the spectroscopic imaging device including at least one of a LCTF and a conformal filter, and operating the LCTF or conformal filter of the spectroscopic imaging device in a pattern of the LCTF or conformal filter in the marker so that the spectroscopic imaging device can accurately distinguish between light that has interacted with the conformal filter and light that has not interacted with the marker.

In another embodiment, the marker is illuminated with photons from a light source.

In another embodiment, the light source for illuminating the marker emits spectrum selected from the group consisting of about 180-380 nm (UV), about 700-2500 nm (NIR), about 850-1800 nm (SWIR), about 650-1100 nm (MWIR), about 400-1100 nm (VIS-NIR), about 1200-2450 nm (LWIR), and combinations of the above ranges.

In another embodiment, the illuminating is performed with an external light source.

In another embodiment, the method of covert identification further comprises controlling the LCTF or the conformal filter of the marker with a marker processor.

In another embodiment, the method of covert identification further comprises encrypting the interacted photons with the marker.

In another embodiment, the method of covert identification further comprises controlling the LCTF or the conformal filter of the spectroscopic imaging device with a spectroscopic processor.

In another embodiment, the method of covert identification further comprises decrypting the interacted photons with the spectroscopic imaging device.

In another embodiment, the method of covert identification further comprises supplying power to at least one of the marker or the spectroscopic imaging device.

In another embodiment, the method of covert identification further comprises supplying power to at least one of the marker or the spectroscopic imaging device, and the light source.

In another embodiment, the method of covert identification further comprises identifying friendly persons, vehicles, or buildings based on the interacted photons that were distinguished from other photons that did not interact with the marker.

BRIEF DESCRIPTION OF THE DRAWING

Aspects, features, benefits and advantages of the embodiments described herein will be apparent with regard to the following description, appended claims, and accompanying FIGURE, where the FIGURE is an illustration of a covert identification system according to an embodiment.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

There are several novel embodiments, components, systems, and methods contemplated by the disclosure. In one embodiment, a marker communicates one or more of force identification, force location, force status, target identification, target location, target status, and the like in a manner that is not revealed to broadband sensors. In another embodiment, a spectroscopic imaging device detects the unique spectral profile communicated by the marker. In still another embodiment, a covert identification system includes at least a marker and a spectroscopic imaging device and can be utilized by armed forces to quickly and accurately distinguish friendly, neutral, and civilian forces from enemy or hostile forces. In still another embodiment, a method of covert identification includes interacting with incident photons using a marker to thereby emit a unique spectral profile and detecting the unique spectral profile with a spectroscopic imaging device.

The Marker

A marker interacts with emitted or incident electromagnetic radiation in order to identify various people and objects. The marker is designed to be compact, reliable, use little or no power, and be mounted on any person, vehicle, installation or other object that is to be identified as friendly, neutral, or enemy. The marker should also be low cost. As will be seen below, the goal of the marker is to interact with and reflect incident light, but to do so in a way that renders the marker undetectable to conventional broadband sensors that are available on the market and which are used by enemy forces.

The marker includes tunable filters that interact with incident light that strikes the marker. Such tunable filters are selected from the group consisting of a liquid crystal tunable filter, an acousto tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, a multi-conjugate filter (MCF), a conformal filter, and combinations thereof.

The marker can interact with any spectrum of light including ultraviolet (UV), visible (VIS), near infrared (NIR), short-wave infrared (SWIR), mid infrared (MIR), long wave infrared (LWIR) wavelengths, and some overlapping ranges. These correspond to wavelengths of about 180-400 nm (UV), about 400-700 nm (VIS), about 700-2500 nm (NIR), about 850-1800 nm (SWIR), about 650-1100 nm (MWIR), about 400-1100 nm (VIS-NIR) and about 1200-2450 nm (LWIR). The marker may interact with each of these wavelength ranges individually or in combination of more than one of the listed wavelength ranges.

In some embodiments, the marker interacts with light that is not visible to the human eye so as to remain covert. Such wavelengths include ultraviolet (UV), near infrared (NIR), short-wave infrared (SWIR), mid infrared (MIR), long wave infrared (LWIR) wavelengths, and some overlapping ranges. These correspond to wavelengths of about 180-380 nm (UV), about 700-2500 nm (NIR), about 850-1800 nm (SWIR), about 650-1100 nm (MWIR), and about 1200-2450 nm (LWIR). The marker may interact with each of these wavelength ranges individually or in combination of more than one of the listed wavelength ranges. Of course, in situations where the human eye would not be expected or capable of detecting even a visible light emission, the marker can utilize visible light.

The interaction of the marker with one or more of the above wavelengths may result in the reflection of a subset of the light that was incident on the marker. In one non-limiting example, incident SWIR light is processed by the tunable filter of the marker and reflected as a narrow band of light with a wavelength of about 1340-1350 nm. Similar behavior may be achieved for any other light wavelength range.

In some embodiments, the marker only interacts with selected wavelength ranges. In one embodiment, the marker only interacts with VIS light. In another embodiment, the marker only interacts with NIR light. In another embodiment, the marker only interacts with SWIR light. In another embodiment, the marker only interacts with LWIR light. In another embodiment, the marker interacts only interacts with VIS-NIR light. In some embodiments, at least one of the ranges in the foregoing paragraph are combined, for example, VIS-NIR light and LWIR light.

In some embodiments, the marker is controlled by a marker processor that operates the marker using wavelength hopping techniques in order to present a unique spectral profile. During operation, the marker processor controls the marker's emission of light spectrum so that it rapidly switches the signal carrier, or band, among multiple wavelengths of light. The switching of the signals among multiple wavelengths of light is performed according to a sequence that is known only to the members and equipment of friendly forces. In some embodiments, a pattern of wavelength switching is performed via a pseudorandom sequence that is designed to appear random or "noisy" to enemy sensors and equipment. By using a pseudorandom sequence for the wavelength hopping operations, the spectral profile presented by the marker is likely to be mistaken for signal noise or some other signal that is to be discarded. This is especially useful in covert conditions such as at night, where all sensors struggle to detect optical signals. In such operating conditions, signal processors often deploy aggressive noise reduction algorithms to reduce unwanted background image noise that is detected by optical sensors. The use of a pseudorandom sequence combined with low emissions amplitudes increases the chance that enemy broadband sensors will fail to detect or will overlook the marker's emissions, thus protecting the location and identity of friendly forces. The above pseudorandom sequence may be defined by an encrypted number sequence that is known to friendly forces.

Separate and in addition to the above wavelength hopping capabilities, the optical wavelengths may be used to communicate an encrypted signal. The encrypted signal may obscure information that is being carried by the emissions from the marker, such as the identity or status of the personnel that are wearing the marker. By encrypting the content of the signal, even if enemy forces somehow manage to discover the presence of the signal by defeating the wavelength hopping techniques, they still cannot decrypt the information without the necessary encryption keys. The encryption algorithm employed is not limited and may include one or more of Triple Data Encryption Standard (3DES), Twofish, Rivest-Shamir-Adleman (RSA), and Advanced Encryption Standard (AES). Whatever the selected encryption algorithm, the disclosure contemplates that it may be symmetric encryption where the same key is used to both encrypt and decrypt the information and/or asymmetric encryption, where a mixture of public and private keys are used to encrypt and decrypt the information. In some embodiments, the encrypted signal is generated when the marker processor controls the behavior of at least one of the LCTF and the conformal filter to alter the optical wavelengths.

In some embodiments, the marker itself includes no independent powered lighting, and is only visible when illuminated externally, such as by sunlight, moonlight, artificial lighting, or combinations of the above. In other embodiments, the marker itself includes internal lighting which can be activated automatically by the marker processor, manually by user intervention, or by a combination of the above. In some embodiments, the illumination is controlled by the marker processor to coincide with, or be synchronized with wavelength hopping capabilities and/or the encryption algorithm. Included powered lighting may be of any design including incandescent lamp, halogen lamp, light emitting diode (LED), chemical laser, solid state laser, organic light emitting diode (OLED), electroluminescent device, fluorescent lamp, gas discharge lamp, metal halide lamp, xenon ark lamp, induction lamp, or any combination of these light sources. The illumination may be any useful spectrum including ultraviolet (UV), visible (VIS), near infrared (NIR), short-wave infrared (SWIR), mid infrared (MIR), long wave infrared (LWIR) wavelengths, and any overlapping ranges. These correspond to wavelengths of about 180-380 nm (UV), about 380-700 nm (VIS), about 700-2500 nm (NIR), about 850-1800 nm (SWIR), about 650-1100 nm (MWIR), about 400-1100 nm (VIS-NIR) and about 1200-2450 nm (LWIR). The wavelengths may be used alone or in combinations of the above.

In some embodiments, the marker receives electrical power from an external or internal power source. The external or internal power source is not limited and may be an electrical system of a vehicle, an electrochemical cell or battery of cells, an electrochemical fuel cell or battery of fuel cells, a mechanical generator, a photovoltaic cell, a thermoelectric generator, or any combinations of the above. In some embodiments, the electrochemical cells or batteries of cells may be selected from any chemistry including nickel metal hydride, nickel cadmium, lithium ion, lithium polymer, lithium, alkaline, silver oxide, hydrogen fuel cell, direct methanol fuel cell, or any combination of the above. The above electrochemical cells may be primary cells, secondary cells, fuel cells, or any combinations of the above.

The marker can be applied to or used by any person, structure, vehicle, materiel (supplies), targets, friendly forces, neutral forces, enemy targets, or civilians, though this list is not limiting and other categories of people and objects both in theaters of war and/or in peacetime scenarios are contemplated here. It is contemplated that the marker is small enough to be included as a patch on a person's clothing or uniform, and that it can be mounted on buildings, installations, vehicles, bags, pallets, packs, and the like.

The spectral profile of the marker can be configured to present a wide range of information. In some embodiments, the spectral profile provides information about the identity of the holder of the marker, such as friendly forces, neutral forces, coalition partners, civilians, enemy forces, friendly structure, or enemy structure. In some embodiments, the spectral profile provides information about the status of the holder, such as whether the holder has been injured or is incapacitated, whether the holder is ready to advance, or whether the holder requires assistance.

The Spectroscopic Imaging Device

At least one spectroscopic imaging device is designed to function in concert with the above-described markers in order to locate and identify various other forces in the theater of war and/or in peacetime scenarios. The spectroscopic imaging device is a hyperspectral imaging device that permits images to be collected at various wavelengths. In some embodiments, the spectroscopic imaging device is a liquid crystal tunable filter (LCTF). A LCTF uses birefringent retarders to distribute the light energy of an input light signal over a range of polarization states. The polarization state of light emerging at the output of the LCTF is caused to vary as a function of wavelength due to differential retardation of orthogonal components of the light contributed by the birefringent retarders. The LCTF discriminates for wavelength-specific polarization using a polarizing filter at the output. The polarizing filter passes the light components in the output that are rotationally aligned to the polarizing filter. The LCTF is tuned by adjusting the birefringence of the retarders so that a specific discrimination wavelength emerges in a plane polarized state, aligned to the output polarizing filter. Other wavelengths that emerge in other polarization states and/or alignments are attenuated.

Alternatively, other components may be used instead of or in combination with the LCTF. Such tunable filters include an acousto tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, a multi-conjugate filter (MCF) and combinations thereof. The above filters along with the initially mentioned LCTF may be used alone or in combination.

In other embodiments, the spectroscopic imaging device includes a conformal filter. Conformal filters may include tunable filters, which are traditionally intended for single bandpass transmission, and are designed to enable tuning to a plurality of different configurations. This is particularly useful when detecting the wavelength hopping spectral profile is described throughout the specification.

U.S. Patent Application Publication Number 2014/0198315 to Treado et al., filed Jan. 15, 2014 assigned to ChemImage Corporation and entitled SYSTEM AND METHOD FOR ASSESSING ANALYTES USING CONFORMAL FILTERS AND DUAL POLARIZATION discloses the use of conformal filters in a dual polarization configuration as discussed above and is incorporated by reference herein in its entirety.

The filters of the spectroscopic imaging device are provided in combination with a detector that detects photons that pass through the filters. The detector or combination of detectors must accurately identify photons of a wide variety of wavelengths. The wavelengths that are to be identified include ultraviolet (UV), visible (VIS), near infrared (NIR), short-wave infrared (SWIR), mid infrared (MIR), long wave infrared (LWIR) wavelengths, and some overlapping ranges. These correspond to wavelengths of about 180-380 nm (UV), about 380-700 nm (VIS), about 700-2500 nm (NIR), about 850-1800 nm (SWIR), about 650-1100 nm (MWIR), about 400-1100 nm (VIS-NIR) and about 1200-2450 nm (LWIR). One more detectors may be included to detect one or more of the above listed wavelengths.

In some embodiments, the spectroscopic imaging device only interacts with selected wavelength ranges. In one embodiment, the marker only interacts with VIS light. In another embodiment, the marker only interacts with NIR light. In another embodiment, the marker only interacts with SWIR light. In another embodiment, the marker only interacts with LWIR light. In another embodiment, the marker interacts only interacts with VIS-NIR light. In some embodiments, at least one of the ranges in the foregoing paragraph are combined, for example, VIS-NIR light and LWIR light.

In one embodiment, the detector is selected from a group consisting of a charged coupled device (CCD) detector, a complementary metal oxide semiconductor (CMOS) detector, an indium gallium arsenide (InGaAs) detector, a platinum silicide (PtSi) detector, a mercury cadmium telluride (HgCdTe) detector, a colloidal quantum dot (CQD) detector, an indium antimonide (InSb) detector and combinations thereof.

In one embodiment, the spectroscopic imaging device includes a spectroscopic processor in communication with the detector and the filters. The spectroscopic processor simultaneously receives a signal from the detector and controls the tunable filter so that the two act in concert with respect to receiving an optical signature from at least one marker. Because the marker employs various techniques to hide its location and identity from enemy forces, such as wavelength hopping and encryption, the spectroscopic processor in conjunction with the detector and the filters must be configured to synchronize with the marker in order to properly detect the presence of the marker.

In one embodiment, in addition to processing the signal from the detector and controlling the tunable filter, the spectroscopic processor is configured to integrate the information from the detector into an image generated by other optical devices. For example, the spectroscopic processor may integrate information from the spectroscopic device with the information from a night vision device. The combination of useful, real-time information about the user's surroundings as well as the identity and other information about other users of the marker device results in a useful enhancement on war theater visual information.

In one embodiment, the spectroscopic processor operates the spectroscopic imaging device so that the spectroscopic imaging device uses wavelength hopping techniques in synchronization with the marker. This enables the spectroscopic device to detect the unique spectral profile that is generated by the marker. During operation the spectroscopic processor controls the detector, the tunable or conformal filters, or other components of the spectroscopic imaging device so that it can detect the switching of signals that are known only to the members and equipment of friendly forces. Similar to the above description with respect to the marker, in some embodiments, a pattern of wavelength switching is performed via a pseudorandom sequence that is designed to appear random or "noisy" to enemy sensors and equipment. Even though the marker presents a pseudorandom sequence for the wavelength hopping operations, this spectral profile is still easily recognized by the spectroscopic imaging device.

Separate and in addition to the above wavelength hopping capabilities, the spectroscopic imaging device is capable of decrypting an encrypted signal. In some embodiments, the decryption is performed by the spectroscopic processor, typically after the signal has been processed from the optical signal hopping described above. The decryption of the signal results in the spectroscopic imaging device and the spectroscopic processor identifying the location, identity, or other information associated with the marker, even in difficult conditions such as low light. As above, the encryption algorithm that is decrypted by the spectroscopic processor is not limited and may include one or more of Triple Data Encryption Standard (3DES), Twofish, Rivest-Shamir-Adleman (RSA), and Advanced Encryption Standard (AES). More generally, the selected encryption algorithm may be symmetric encryption algorithm, where the same key is used to both encrypt and decrypt the information and/or an asymmetric encryption, where a mixture of public and private keys are used to encrypt and decrypt the information. In some embodiments, the decrypting of the encrypted signal is performed when the spectroscopic imaging processor controls the behavior of at least one of the LCTF and the conformal filter to alter the optical wavelengths.

In some embodiments, the spectroscopic imaging device receives electrical power from an external or internal power source. The external or internal power source is not limited and may be an electrical system of a vehicle, an electrochemical cell or battery of cells, an electrochemical fuel cell or battery of fuel cells, a mechanical generator, a photovoltaic cell, a thermoelectric generator, or any combinations of the above. In some embodiments, the electrochemical cells or batteries of cells may be selected from any chemistry including nickel metal hydride, nickel cadmium, lithium ion, lithium polymer, lithium, alkaline, silver oxide, hydrogen fuel cell, direct methanol fuel cell, or any combination of the above. The above electrochemical cells may be primary cells, secondary cells, fuel cells, or any combinations of the above.

In some embodiments, the spectroscopic imaging device includes no independent powered lighting, and thus can only passively observe objects that are illuminated externally, such as by sunlight, moonlight, artificial lighting, and combinations of the above. In other embodiments, the spectroscopic imaging device includes or is closely associated or closely mounted with lighting that can be activated automatically by the spectroscopic processor, manually by user intervention, or combinations of the above. In some embodiments, the illumination is controlled by the spectroscopic processor to coincide with, or be synchronized with, wavelength hopping capabilities and/or the encryption algorithm. Included powered lighting may be of any design including incandescent lamp, halogen lamp, light emitting diode (LED), chemical laser, solid state laser, organic light emitting diode (OLED), electroluminescent device, fluorescent lamp, gas discharge lamp, metal halide lamp, xenon ark lamp, induction lamp, or any combination of these light sources. The powered lighting may emit ultraviolet (UV), visible (VIS), near infrared (NIR), short-wave infrared (SWIR), mid infrared (MIR), long wave infrared (LWIR) wavelengths, and any overlapping ranges. These correspond to wavelengths of about 180-380 nm (UV), about 380-700 nm (VIS), about 700-2500 nm (NIR), about 850-1800 nm (SWIR), about 650-1100 nm (MWIR), about 400-1100 nm (VIS-NIR) and about 1200-2450 nm (LWIR). In some embodiments, the wavelength emitted by the powered lighting may be encompassed by one or more of these ranges.

The spectroscopic imaging device can be mounted on or used by any person, structure, vehicle, or weapons system so that the identity, location, status, and other information being transmitted by the markers can be identified. The physical size of the spectroscopic imaging device is not limited, but small sizes are particularly useful so that portability and space savings are enhanced. In some embodiments, the spectroscopic imaging device is in the form of a prismatoid, parallelepiped, cuboid, rectangular prism, or cube with each side being about 0.5 inches to about 5 inches in length. In one embodiment the spectroscopic imaging device is a prismatoid, rectangular prism, or cube where each side is about 1 inch in length.

Other Components

In addition to the marker and spectroscopic imaging device disclosed above, other components may be provided that improve or add to the functionality of the marker and spectroscopic imaging device.

In some embodiments, the spectroscopic imaging device is associated with a display, goggles, or other eyepiece that is designed to show the images discerned by the spectroscopic imaging device. In some embodiments, the marker or the spectroscopic imaging device is associated with a network interface that permits communication between groups of markers and/or groups of spectroscopic imaging devices, as well as wider military communications networks and all devices attached to such networks. In some embodiments, the spectroscopic imaging device is associated with night imaging equipment that permits the information discerned by the spectroscopic imaging device to be integrated or combined with other critical visual information, such as night vision imagery and thermal imagery.

EXAMPLES

A non-limiting Example was constructed to demonstrate one embodiment of the disclosure and is shown schematically in the FIGURE. First, an optical breadboard (not shown) was constructed for mounting and positioning the various components to form a covert imaging system 1. On the optical breadboard, an infrared light source 2 was placed comprising an infrared filtered flashlight (i.e., the flashlight emits infrared radiation by filtering out other spectra). The infrared filtered flashlight was pointed towards a section of camouflaged cloth 3 representing the uniform of friendly forces. The section of camouflaged cloth 3 contained a cutout exposing a conformal filter placed in front of a reflector, where the combination of the cutout, conformal filter, and reflector collectively form the marker 4. The marker 4 was configured to emit a unique spectral profile by way of reflecting and interacting with the photons from the infrared light source 2.

The optical breadboard and covert imaging system 1 also includes first decoding conformal filter 5 and second decoding conformal filter 6 that receive the reflected light 7 through a beam splitter 8 and associated optical components such as lenses and mirrors. As a result of these optical paths, each of the first decoding conformal filter 5 and the second decoding conformal filter 6 produces respective images 9 and 10. The respective images 9 and 10 are analyzed using image math by a processor (not shown) to yield a final detected image 11 which clearly shows the location of the marker 4 on the camouflaged cloth 3 (the location is shown in the drawing as a white square). The overall covert imaging system is capable of real-time detection, with frame rates greater than about 10 frames per second when a dual polarization optical subsystem is selected. Because the image is only generated when the first and second decoding conformal filters 5 and 6 are tuned by the processor to correspond to the pre-determined state of the marker 4, the reflection from the marker 4 is only detectable by applying image math to the first and second images 9 and 10. A conventional broadband sensor (not shown) cannot detect the presence of the marker 4 because conventional broadband sensors are unable to detect the fine level of contrast present between light that is attributed to the marker 4 and light that is attributed to the camouflaged cloth 3 when such sensors image the reflected light. Thus, covert imaging system 1, by using the first decoding conformal filter 5 and the second decoding conformal filter 6, quickly and accurately distinguishes between light reflected by the marker 4 and by the camouflaged cloth 3.

In a further modification of the above Example, the marker 4 was configured to reflect the light from the infrared light source 2 in a pre-determined multi-band waveform, which results in an encrypted signal. The encrypted signal is then decrypted when the processor performs image math and controls the conformal filters 5 and 6 which results in the final detected image 9. Again, this results in a final detected image 9 that is achievable only via the covert identification system of the disclosure.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the FIGURES, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:
1. A covert identification system comprising:
   a marker that includes at least one of a liquid crystal tunable filter (LCTF) and a conformal filter and which reflects interacted photons that have interacted with the LCTF or the conformal filter,
   a spectroscopic imaging device that includes a spectroscopic processor and at least one of a LCTF and a conformal filter and which is configured to receive the interacted photons, and
   wherein the spectroscopic processor operates at least one of the LCTF or conformal filter of the spectroscopic imaging device in a pattern of wavelength switching that corresponds to a pattern of wavelength switching of the LCTF or conformal filter in the marker so that the spectroscopic imaging device can accurately distin- guish between light that has interacted with the LCTF or conformal filter and light that has not interacted with the marker.

2. The covert identification system of claim 1, further comprising a light source that is configured to illuminate the marker.

3. The covert identification system of claim 2, wherein the light source for illuminating the marker emits spectrum selected from the group consisting of about 180-380 nm (UV), about 700-2500 nm (NIR), about 850-1800 nm (SWIR), about 650-1100 nm (MWIR), about 400-1100 nm (VIS-NIR), about 1200-2450 nm (LWIR), and combinations of the above ranges.

4. The covert identification system of claim 1, wherein the covert identification system does not include a light source for illuminating the marker, and during operation, the marker is illuminated by an external light source.

5. The covert identification system of claim 1, the marker further including a marker processor that is configured to control at least one of the LCTF or the conformal filter of the marker.

6. The covert identification system of claim 5, wherein the marker processor is configured to control at least one of the LCTF or the conformal filter of the marker to thereby encrypt the interacted photons.

7. The covert identification system of claim 1, wherein the spectroscopic processor is configured to control at least one of the LCTF or the conformal filter of the spectroscopic imaging device to thereby decrypt the interacted photons.

8. The covert identification system of claim 1, further comprising a power source.

9. A method of covert identification comprising:
   illuminating with photons a marker that includes at least one of a liquid crystal tunable filter (LCTF) and a conformal filter so that the marker reflects interacted photons that have interacted with the LCTF or the conformal filter,
   receiving interacted photons with a spectroscopic imaging device, the spectroscopic imaging device including a spectroscopic processor and at least one of a LCTF and a conformal filter, and
   operating, with the spectroscopic processor, the LCTF or conformal filter of the spectroscopic imaging device in a pattern of wavelength switching that corresponds a pattern of wavelength switching of the LCTF or conformal filter in the marker so that the spectroscopic imaging device can accurately distinguish between light that has interacted with the LCTF or conformal filter and light that has not interacted with the marker.

10. The method of claim 9, wherein the marker is illuminated with photons from a light source.

11. The method claim 10, wherein the light source for illuminating the marker emits spectrum selected from the group consisting of about 180-380 nm (UV), about 700-2500 nm (NIR), about 850-1800 nm (SWIR), about 650-1100 nm (MWIR), about 400-1100 nm (VIS-NIR), about 1200-2450 nm (LWIR), and combinations of the above ranges.

12. The method of claim 10, wherein the illuminating is performed with an external light source.

13. The method of claim 9, further comprising controlling the LCTF or the conformal filter of the marker with a marker processor.

14. The method of claim 13, further comprising encrypting the interacted photons with the marker.

15. The method of claim 9, further comprising decrypting the interacted photons with the spectroscopic imaging device.

16. The method of claim 9, further comprising supplying power to at least one of the marker or the spectroscopic imaging device.

17. The method of claim 16, further comprising supplying power to at least one of the marker or the spectroscopic imaging device, and an external light source.

18. The method of claim 9, further comprising identifying friendly persons, vehicles, or buildings based on the interacted photons that were distinguished from other photons that did not interact with the marker.

* * * * *